United States Patent
Pesenti et al.

(10) Patent No.: US 10,953,175 B2
(45) Date of Patent: Mar. 23, 2021

(54) APPARATUS FOR CONTROLLING THE PRESSURE IN AN ENDOTRACHEAL CUFF, POSITIVE-PRESSURE VENTILATOR FOR ARTIFICIAL VENTILATION OF AN INTUBATED PATIENT AND METHOD FOR MANAGING SECRETIONS IN AN INTUBATED PATIENT

(71) Applicant: UNIVERSITA' DEGLI STUDI DI MILANO-BICOCCA, Milan (IT)

(72) Inventors: Antonio Maria Pesenti, Milan (IT); Alberto Zanella, Lissone (IT); Luigi Castagna, Lissone (IT); Vittorio Scaravilli, Monza (IT)

(73) Assignee: AW TECHNOLOGIES APS, Nørre Sundby (DK)

( * ) Notice: Subject to any disclaimer, the term of this patent is extended or adjusted under 35 U.S.C. 154(b) by 394 days.

(21) Appl. No.: 15/573,768

(22) PCT Filed: May 18, 2016

(86) PCT No.: PCT/IB2016/052894
§ 371 (c)(1),
(2) Date: Nov. 13, 2017

(87) PCT Pub. No.: WO2016/189427
PCT Pub. Date: Dec. 1, 2016

(65) Prior Publication Data
US 2018/0126105 A1    May 10, 2018

(30) Foreign Application Priority Data
May 25, 2015   (IT) .................. 102015000017412

(51) Int. Cl.
*A61M 16/04*    (2006.01)
*A61M 16/00*    (2006.01)
*A61M 16/20*    (2006.01)

(52) U.S. Cl.
CPC ...... *A61M 16/044* (2013.01); *A61M 16/0445* (2014.02); *A61M 16/0488* (2013.01);
(Continued)

(58) Field of Classification Search
CPC ............ A61M 16/044; A61M 16/0445; A61M 16/045; A61M 16/0488; A61M 16/0479; A61M 2016/0027; A61M 2205/07
See application file for complete search history.

(56) References Cited

U.S. PATENT DOCUMENTS 5,235,973 A    8/1993  Levinson
5,819,723 A    10/1998 Joseph
(Continued)

FOREIGN PATENT DOCUMENTS

WO    WO0100267 A1    1/2001

OTHER PUBLICATIONS

International Search Report and Written Opinion dated Aug. 12, 2016 for counterpart PCT Application No. PCT/IB2016/052894.

*Primary Examiner* — Samchuan C Yao
*Assistant Examiner* — Nathan M Le
(74) *Attorney, Agent, or Firm* — Shuttleworth & Ingersoll, PLC; Timothy J. Klima

(57) ABSTRACT

A method for the management of secretions in an intubated patient by means of an endotracheal tube to which an inflatable cuff is externally associated, includes the steps of inflating the inflatable cuff for isolating the broncho-pulmonary zone of the patient from the external environment, generating a succession of overpressures inside the endotracheal tube in order to induce breathing in the patient, and (Continued)

a step of deflating the inflatable cuff during the generation of one of the overpressures in order to permit a drainage of the secretions generated by the patient along the trachea towards the outside.

20 Claims, 6 Drawing Sheets

(52) U.S. Cl.
CPC ....... *A61M 16/0479* (2014.02); *A61M 16/201* (2014.02); *A61M 2016/0027* (2013.01); *A61M 2205/07* (2013.01); *A61M 2205/50* (2013.01)

(56) References Cited

U.S. PATENT DOCUMENTS

| | | |
|---|---|---|
| 2011/0178419 A1 | 7/2011 | Wood et al. |
| 2011/0197888 A1* | 8/2011 | Deutsch ............ A61M 16/0479 128/204.23 |
| 2014/0137867 A1 | 5/2014 | Pacey |
| 2014/0366874 A1* | 12/2014 | Deutsch ............ A61M 16/0479 128/202.13 |

* cited by examiner

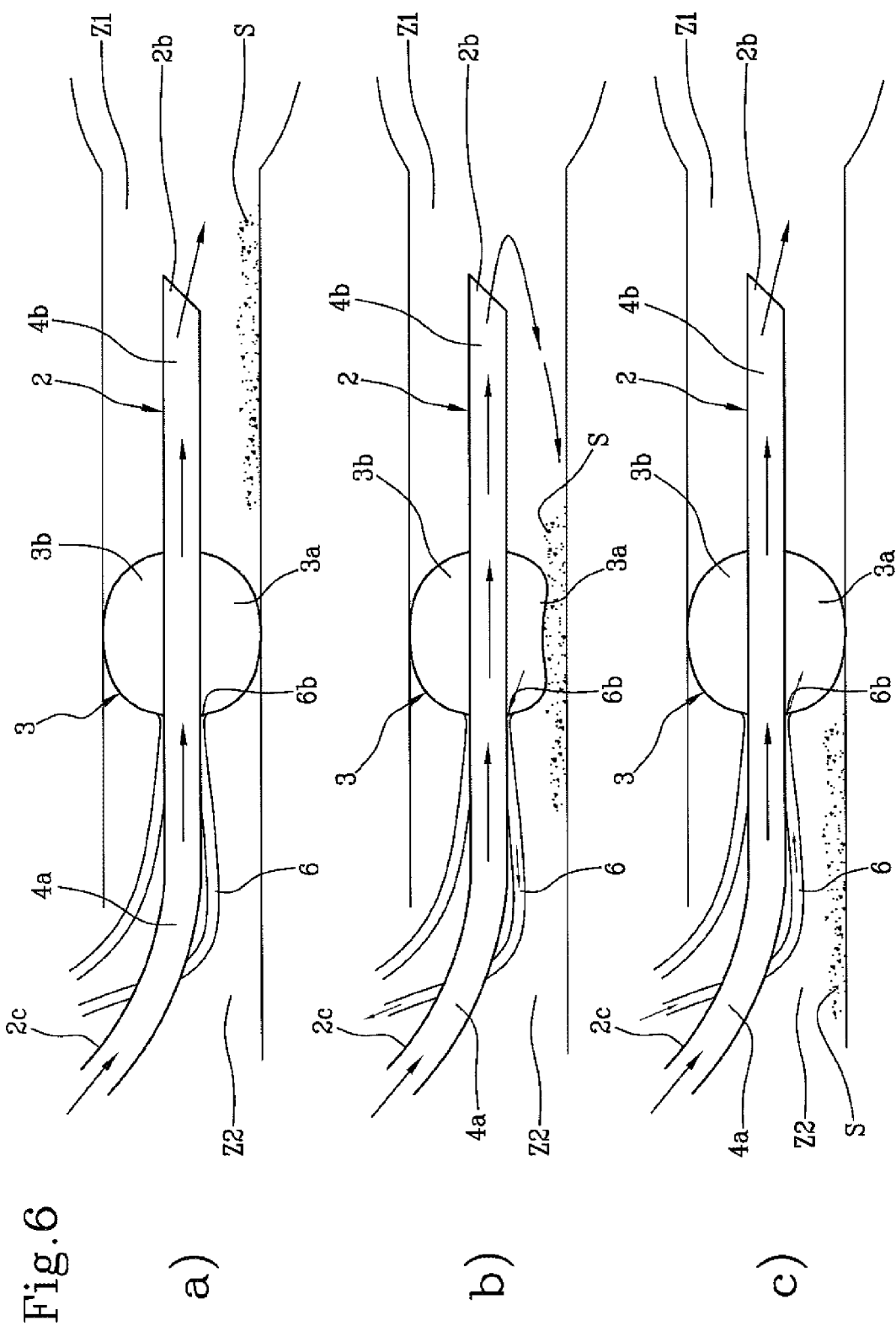

APPARATUS FOR CONTROLLING THE PRESSURE IN AN ENDOTRACHEAL CUFF, POSITIVE-PRESSURE VENTILATOR FOR ARTIFICIAL VENTILATION OF AN INTUBATED PATIENT AND METHOD FOR MANAGING SECRETIONS IN AN INTUBATED PATIENT

This application is the National Phase of International Application PCT/IB2016/052894 filed May 18, 2016 which designated the U.S.

This application claims priority to Italian Patent Application No. 102015000017412 filed May 25, 2015, which application is incorporated by reference herein.

The present invention refers to an apparatus for controlling the pressure in an endotracheal cuff, positive-pressure ventilator for artificial ventilation of an intubated patient and method for managing secretions in an intubated patient.

The present invention finds particular application in the production of medical apparatuses, in particular in the realization of devices for forced ventilation.

More particularly, the present invention is arranged to be exploited for patients provided with respiratory prostheses and/or for artificially ventilated patients.

As know, ventilated patients (particularly those who are in intensive therapy) find it difficult to clear secretions from the respiratory tract since the presence of the endotracheal tube and the relative sealing cuff prevent what is commonly known as "mucociliary clearance", i.e., the natural mechanism that allows the automatic expulsion of secretions through the ascent action of the same along the walls of the airways by ciliated epithelium.

To date, the only known techniques for the removal of these secretions are of the manual type, which are however invasive in nature, since they require that the medical personnel and/or nursing staff carry out the removal of the same by means of a procedure called tracheal-bronchoaspiration, tracheal aspiration or tracheobronchial aspiration. This procedure involves inserting a conduit or catheter (suction tube) inside the airway of the patient, through the endotracheal tube, and aspiring these secretions, allowing the patient to ventilate properly.

Disadvantageously, this procedure has considerable drawbacks, both from the point of view of effectiveness and from the point of view of invasiveness.

In fact, for years it is known that, despite the state of altered consciousness, the tracheal-bronchoaspiration is one of the few moments that remain etched in the memories of treated patients because of the pain felt.

Moreover, given that the conduit must be inserted into the endotracheal tube in order to reach the lower airways, the large amount of secretions that are present between the free end of the tube and the cuff are not reachable from the conduit itself, and are not therefore aspirated, which can therefore accumulate and remain in the airways for a long time.

Obviously, these remained secretions may induce alterations of the respiratory, cardiovascular and metabolic functions of the patient, as manifested by a reduction in blood oxygen saturation, increased respiratory rate and respiratory fatigue, experience of episodes of high blood pressure, tachycardia, disorders of acid-base balance, increase in basal metabolism, and other complications known to specialists.

A further and more recently solution is known from the document US 2014/0137867, in which an apparatus is described comprising an endotracheal tube and a cuff disposed around it, in which the cuff has a recess or a peripheral longitudinal groove to define a passage for the secretions and that is adjacent to the wall of the trachea.

Clearly, this solution while permitting, at least theoretically, a "natural" drainage of secretions, introduces a variety of issues and problems within the system.

Primarily, these problems are related to the fact that the presence of the groove makes the cuff permanently permeable, affecting as a result the sterility of the distal zone of the airways.

In other words, the leakage of secretions through the cuff corresponds to a permanent passage of air and bacteria between the zone of the airway that is internal and external to the cuff.

Moreover, the presence of such leakage, in addition to decreasing the efficiency of the ventilator, does not ensures in any way that the secretions are moved from the inside to the outside, but also may cause a reverse passage of substances having a bacterial load.

The object of the present invention is therefore to make available a method for the management of secretions in an intubated patient, an apparatus for controlling the pressure in an endotracheal cuff, a positive-pressure ventilator for artificial ventilation of an intubated patient, which are able to solve and overcome the prior art drawbacks mentioned above.

In particular, object of the present invention is to make available a method for the management of secretions in an intubated patient, an apparatus for controlling the pressure in an endotracheal cuff and a positive-pressure ventilator for artificial ventilation of an intubated patient, which provide an efficient evacuation of secretions produced by the patient.

More precisely, the purpose of the present invention is to make available a method for the management of secretions in an intubated patient that is little invasive and highly efficient.

In addition, it is object of the present invention to make available an apparatus for controlling the pressure in an endotracheal cuff and a positive-pressure ventilator for artificial ventilation of an intubated patient that is constructively simple and minimizes the intervention of the personnel.

These and other objects are achieved by an apparatus for controlling the pressure in an endotracheal cuff having features as disclosed herein, by a positive-pressure ventilator for artificial ventilation of an intubated patient having features as disclosed herein, and by a method for the management of secretions in an intubated patient having features as disclosed herein.

In particular, these aims are achieved by a method for the management of secretions in an intubated patient comprising the steps of inflating the inflatable cuff to isolate the bronchopulmonary zone of the patient from the outside environment, generating a succession of overpressures inside the endotracheal tube in order to induce breathing in the patient.

According to an aspect of the present invention, the method comprises a step of deflating said inflatable cuff during the generation of one of said overpressures in order to enable drainage of the secretions generated by the patient along the trachea towards the outside.

Preferably, the step of generating a succession of overpressures comprises a step of generating a cyclical succession of first overpressures inside the endotracheal tube in order to induce breathing in the patient and, downstream of one of said first overpressures, a step of generating a second overpressure inside the tube, of a duration and a value exceeding that of said first overpressures, in order to recruit the lung of the patient.

Note that with the expression "recruit the lung" is meant, in the jargon, and therefore in this context, a manoeuvre with the goal of "reopen", via a pressure raising (or sigh), lung areas that otherwise would not be reached by the ventilation.

According to one aspect of the present invention, the step of deflating said inflatable cuff is carried out during said generation of the second overpressure in order to enable drainage of the secretions generated by the patient along the trachea, from the bronchopulmonary zone towards the outside.

Advantageously, such method allows exploiting the overpressure generated during the so-called "sigh" to produce the necessary thrust to ensure the drainage of secretions that, thanks to a temporary and calibrated cuff deflation, exit from broncho-pulmonary zone going up the trachea, exiting therefore from the "distal zone" of the airways.

Note that with the terms "distal" and "proximal", in medical jargon, and therefore in this context, is meant the lower zone (bronchi-lungs) and the upper zone (mouth) of the airways, respectively.

Furthermore, this method can prevent external intervention for the removal of secretions, supporting the mucociliary clearance function.

Note that, preferably, the step of deflating the inflatable cuff starts with a delay equal to a pre-established first time interval, from an initial instant of the step of generation of the second overpressure.

Advantageously, this ensures that the overpressure generated in the endotracheal tube corresponds to a sufficient increase of pressure in the broncho-pulmonary zone, i.e., in the "sterile" zone.

In order to implement a so-structured method, it is possible to provide a special apparatus to be connected with an existing ventilator or integrated into it.

Said apparatus preferably has an endotracheal tube, an inflatable cuff positioned along said tube for subdividing its outer surface in a first portion, proximal in use, and a second portion, distal in use, at least one pressure management unit, placed in fluid connection with said inflatable cuff and selectively switchable between an inflation configuration, in which it inflates and/or maintains inflated the inflatable cuff, and a deflation configuration, wherein it deflates the inflatable cuff, pressure sensing means configured to detect a pressure correlated with or representative of the airway (or pulmonary) pressure of an intubated patient, and at least one control module associated to said management unit and to said sensing means, and configured to control said management unit on the basis of the signal read by said sensing means.

According to an aspect of the present invention, the control module is programmed to switch the management unit into said deflation configuration upon the receipt, by said sensing means, of a signal representative of the exceeding of a pre-established threshold value of said detected pressure in order to enable, outside said tube, a drainage of the secretions generated by the patient from the second portion to the first portion.

Advantageously, in this way it is possible to exploit the knowledge of the pressure signal in the airways, whether it is detected in the ventilator (easier), in the tube or in the broncho-pulmonary zone (more problematic), and control the cuff accordingly, allowing the natural functioning of the mucociliary clearance.

By integrating this apparatus in a known positive-pressure ventilator, said endotracheal tube is connected to said outlet of the overpressure generating means and the control unit is associated with (or includes) the control module in order to control the management unit on the basis of a condition of the generating means.

The control unit is preferably configured to control the generating means so as to generate a succession of overpressures, wherein at least one of said overpressures has a value greater than or equal to said threshold value; said control module being configured to switch the management unit into said deflation configuration when the generating means generates said overpressure.

More preferably, the control unit is configured to control the generating means in a first mode, in which they generate a cyclical succession of first overpressures, and a second mode, in which they generate a second overpressure of a longer duration than said first overpressures and having a greater value than or equal to said threshold value.

In accordance with the method described above, the control module is preferably configured to switch the management unit in said deflation configuration when the generating means are in said second mode.

Advantageously, in this way the method is simple to implement using the structure, known per se, of existing ventilators.

Further characteristics and advantages of the present invention will become apparent from the following illustrative, and therefore not limiting, description of a preferred, and therefore not exclusive, embodiment of a method for the management of secretions in an intubated patient, with an apparatus for controlling the pressure in an endotracheal cuff and a positive-pressure ventilator for artificial ventilation of an intubated patient, as illustrated in the accompanying drawing tables, in which:

FIGS. 6a-6c show the successive steps of the method according to the present invention implemented by means of a further embodiment of the apparatus.

Figure 1:
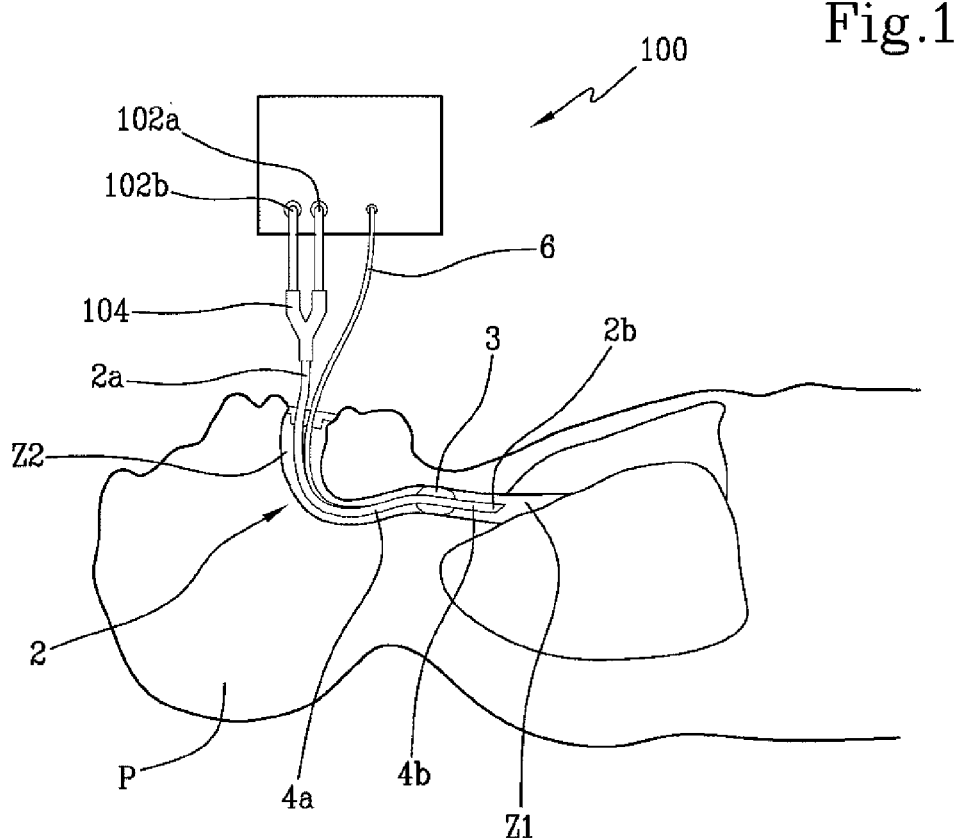
FIG. 1 shows a schematic view of a positive-pressure ventilator according to the present invention, during use.
Figure 1A:
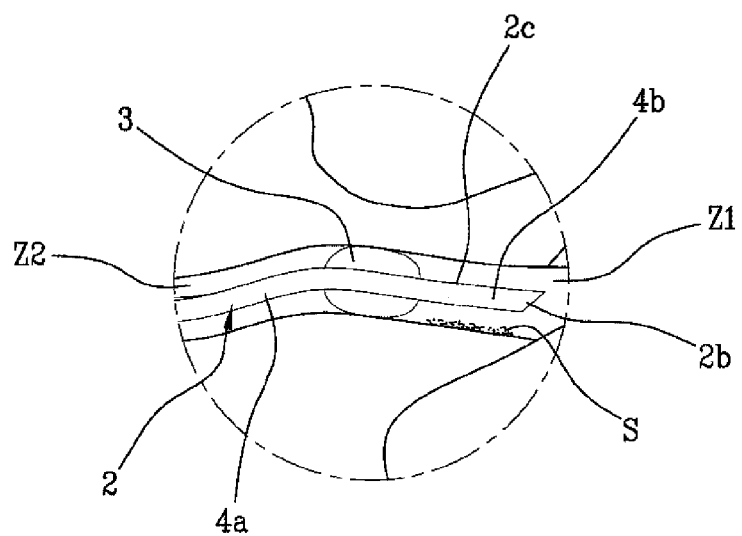
FIG. 1a shows an enlargement of a portion of FIG. 1.

With reference to the attached figures, with the number 1 is hereinafter shown an apparatus for controlling the pressure in an endotracheal cuff according to the present invention.

Such apparatus 1, as already mentioned, is connectable (or connected/integrated) to a positive-pressure ventilator 100 for artificial ventilation of an intubated patient "P".

Therefore, this apparatus 1 comprises an endotracheal tube 2 inserted in the airways of the patient "P".

This tube 2 thus defines an internal cavity delimited by a side wall 2c and extends between a first end 2a, connected to a ventilator 100, and that it is external during use, and a second free end 2b, in use placed in a "distal" position.

The tube 2 is preferably made of PVC or the like.

The tube 2 has an associated inflatable cuff 3.

Such inflatable cuff 3 is a sealing element configured to fit in the internal dimension of the trachea of a patient "P" in order to isolate the distal end (or second end 2b) of the tube from the external environment by allowing the correct operation of the ventilator 100.

The inflatable cuff 3 is thus an annular element externally fitted (and fixed) to the side wall 2c of the tube 2. Therefore, the inflatable cuff 3 divides (externally) the tube 3 in a first portion 4a, in a proximal use, and in a second portion 4b, in a distal use.

The first portion 4a extends from the first end 2a to the cuff 3.

The second portion 4b extends from the cuff 3 to the second end 2b.

Therefore, the cuff 3 has a substantially annular shape (donut-shaped).

As stated above, such cuff 3 is inflatable, therefore has therein a chamber bounded by an outer membrane "M".

Preferably, the outer membrane "M" is made of PVC about 50 microns thick.

Alternatively, the outer membrane "M" is made of polyurethane with a thickness of 7 microns.

Therefore, the cuff 3 (and preferably the chamber) is placed preferably in fluid connection with at least a pressure management unit 5.

In a particular embodiment, the inflatable cuff 3 is divided into a first 3a and a second half-part 3b isolated from each other.

Therefore, the cuff 3 has at least a separation baffle between the first 3a and the second half-part 3b, such as to isolate its contents.

More precisely, the apparatus 1 comprises at least a conduit 6 (having a considerably smaller passage than the tube 2) extending along the tube 2 itself, between its own first external end 6a and its own internal second end 6b, and opening into said chamber.

Preferably, there are two conduits 6 each associated with a half-part 3a, 3b of the cuff 3.

In the preferred embodiment, the conduit 6 is made, or embedded, in the side wall 2c of the endotracheal tube 2, which considerably simplifies the application and use thereof.

The conduit 6 is thus associated to the pressure management unit 5, which is configured to withdraw or pump air into the chamber in order to vary its volume and internal pressure.

More precisely, the pressure management unit 5 is selectively switchable between an inflation configuration, in which it inflates and/or maintains inflated the inflatable cuff 3, and a deflation configuration, wherein it deflates the inflatable cuff 3.

Figure 2:
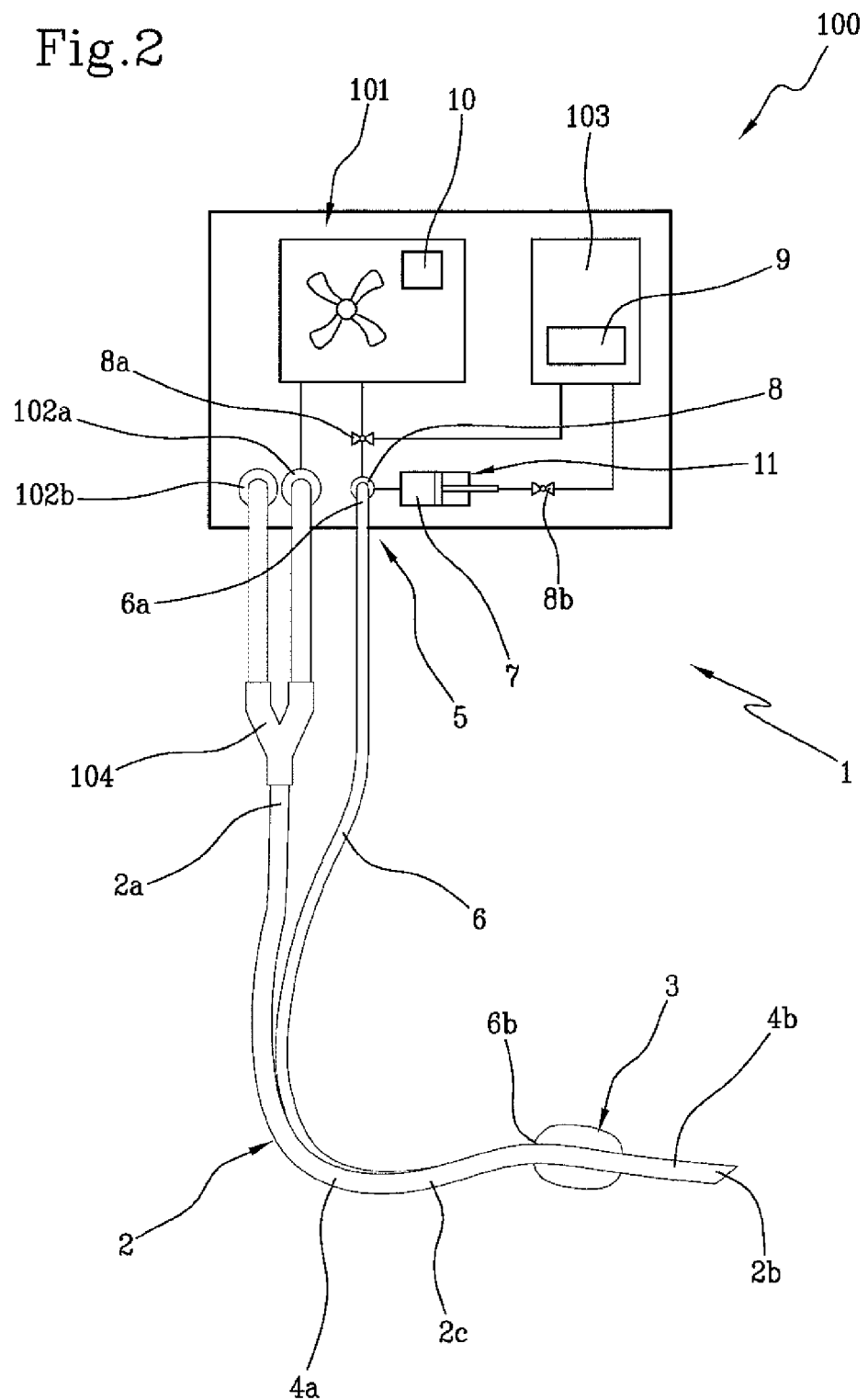
FIG. 2 shows a detailed schematic view of the ventilator of FIG. 1, provided with a first embodiment of an apparatus for controlling the pressure in an endotracheal cuff.

Note that, in a first preferred embodiment (FIG. 2), such a unit may be defined by a volumetric device, capable of aspirating and pumping a predetermined volume of air (or other suitable fluid) from and into the chamber of the cuff 3.

Therefore, in this embodiment, the management unit 5 comprises pumping means adapted to increase the pressure of the cuff to a predetermined value, and an air movement member 11 (preferably a piston) associated with the cuff 3 and the conduit 6, and configured to remove or reintroduce a predetermined volume of air from the cuff 3.

Figure 3:
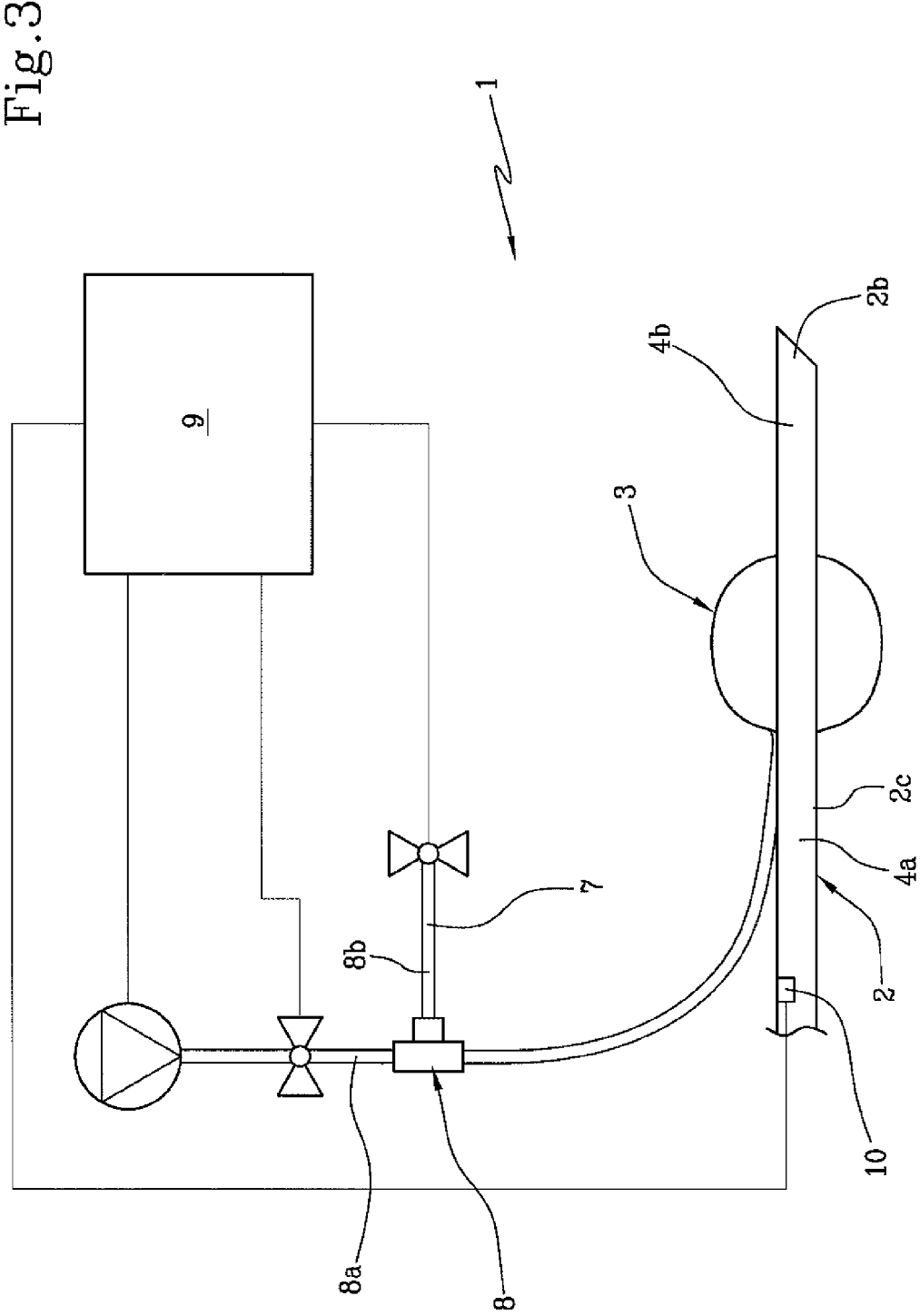
FIG. 3 shows a schematic view of a second embodiment of the apparatus for controlling the pressure in an endotracheal cuff according to the present invention.
Figure 4:
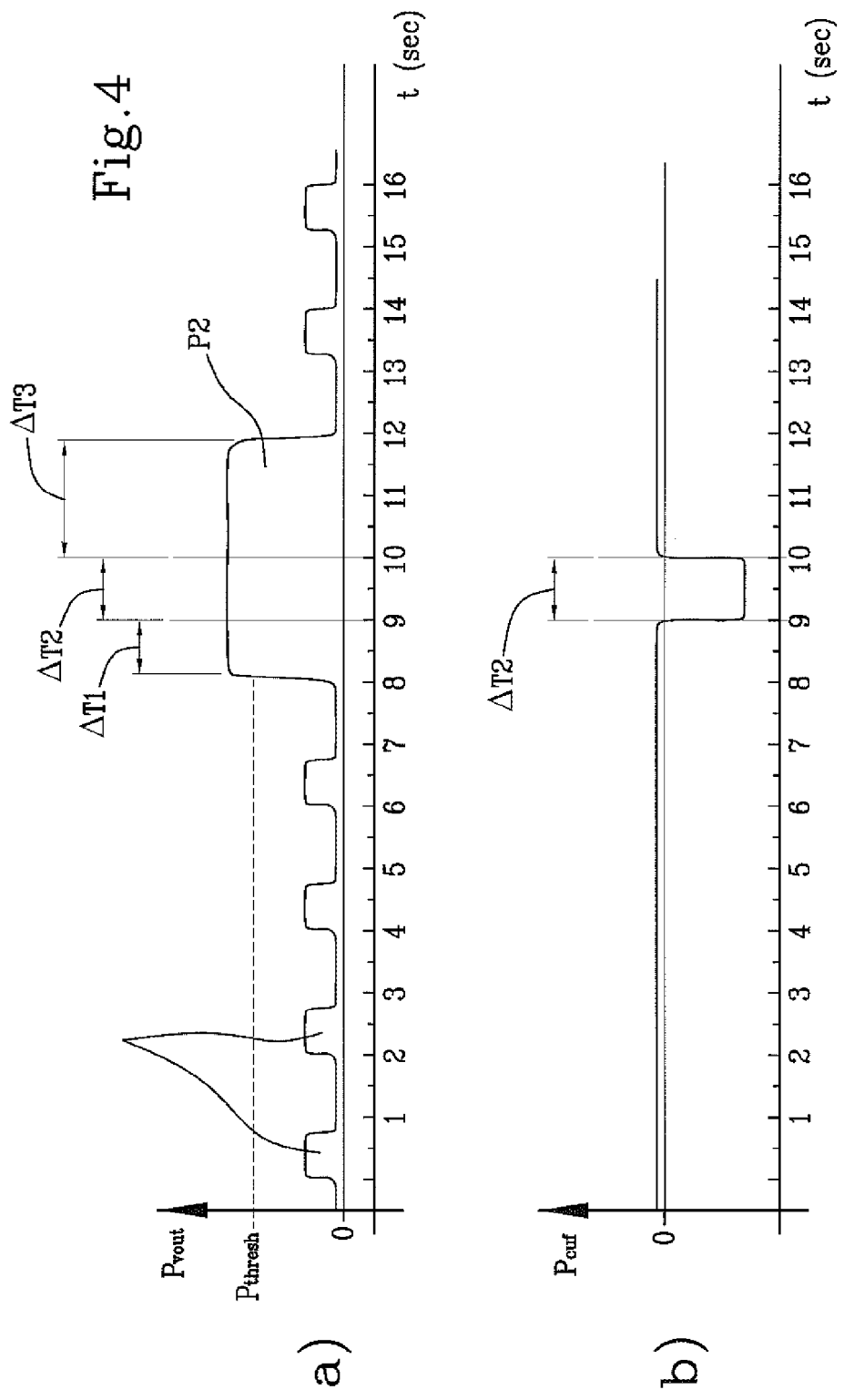
FIGS. 4a and 4b show the trend of the pressures in the airways (ventilator) and in the cuff during the implementation of the method according to the present invention.
Figure 5:
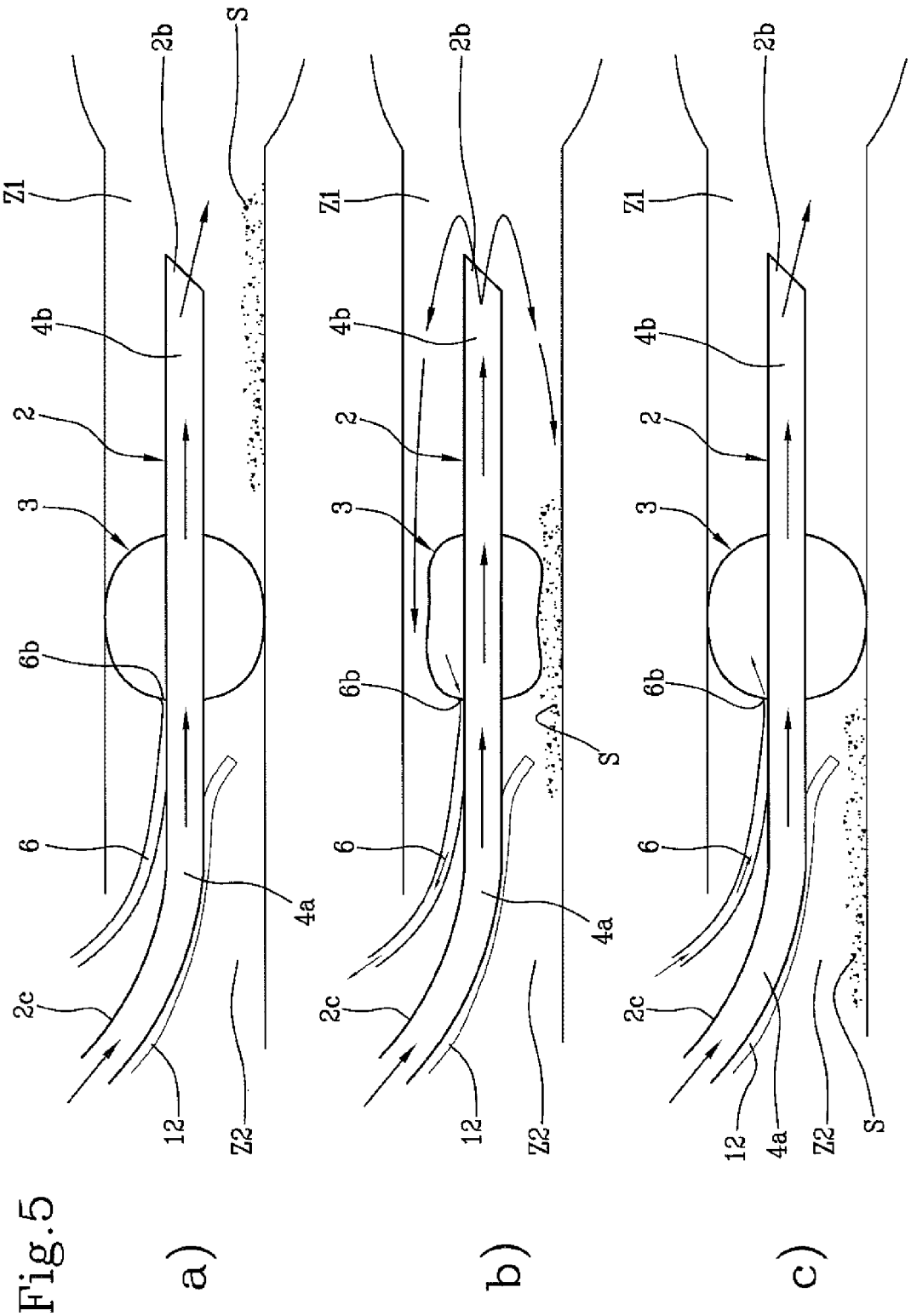
FIGS. 5a-5c show the successive steps of the method according to the present invention.

Alternatively, in the embodiment illustrated in FIG. 3, the management unit 5 can comprise pumping/ventilation means, i.e. means for generating an overpressure operatively associated, in parallel, to a venting conduit 7.

In the illustrated embodiment, the management unit 5 comprises at least one fork 8 placed along the conduit 5.

Such bifurcation 8 defines at least a first branch 8a, connected to said pumping/ventilation means, and a second branch 8b, defining a venting conduit.

In this embodiment, there are valve means configured to open and close selectively said branches 8a, 8b in order to define said inflation and deflation configurations.

Note that, in certain embodiments, there is a detection sensor (not shown) of the pressure inside the cuff 3 (or of a quantity correlated to it).

In this regard, the apparatus comprises at least a control module 9 associated to the management unit 5 and configured to control it through one or more control signals.

In particular, the control module 9 is configured to send to the pumping/ventilation means and to the valve means respective control signals in order to activate or deactivate them according to the configuration, either inflation or deflation configuration, to be established.

In this regard, the apparatus 1 comprises pressure sensing means 10 configured to detect a pressure related to or representative of the pressure of the airways of an intubated patient "P".

Note that, in this context, with the terms "pressure related to or representative of the pulmonary pressure of an intubated patient "P"" is meant to define a pressure value detected, directly or indirectly, along a feed line between the ventilator 100 and the broncho-pulmonary zone downstream of the cuff 3.

More precisely, the presence of the cuff 3 allows to recreate a pressure-tight environment, in which the pressure within the lungs or broncho-pulmonary zone of the patient "P" is determined by the activity of the ventilator 100.

More precisely, the cuff 3 divides the airways of the patient "P" in an isolated zone "Z1", located operatively downstream of the cuff 3 and defined by the broncho-pulmonary zone, and a non-sterile zone "Z2", located between the patient's "P" mouth and the inflatable cuff 3.

Therefore, by detecting the pressure within that environment, between the ventilator itself and the sterile zone (passing through the endotracheal tube 2), it is possible to measure a pressure value, which, except for loss and delay, in other terms the pressure needed to generate the flow, is closely related to the pressure in the broncho-pulmonary zone itself (i.e. in the sterile zone), or the pressure of medical interest to generate the pulmonary ventilation.

In this light, the sensing means 10 can be of a different kind and placed in different positions.

In certain (preferred) embodiments, the sensing means are integrated into the ventilator 100 and operatively connected to the control module 9.

Alternatively, the sensing means 10 are defined by a pressure sensor placed within the endotracheal tube 2, or upstream or downstream of the same.

Preferably, however, the sensing means 10 are directly associated to the ventilator 100, which are means for generating a pressure signal (as will be better clarified in the following); this mainly because the pressure signal generated by the ventilator is more regular and more easily used as a control parameter.

In fact, in this regard it is noted that the control module 9 is configured to control the management unit 5 according to the signal detected by said sensing means 10.

More precisely, according to one aspect of the present invention, the control module 9 is programmed to switch the management unit 5 into said deflation configuration upon the receipt, by said sensing means 10, of a signal representative of the exceeding of a pre-established threshold value Pthresh of the detected pressure.

Advantageously, this to enable, outside said tube 2, a drainage of the secretions S generated by the patient "P" from the second portion 4b to the first portion 4a.

In other words, once exceeded a predetermined reference pressure value, related to or representative of the pressure in the airways, the control module 9 sends to the management unit a signal representative of a deflation condition of the cuff 3.

Therefore, the management module controls the opening of the valve of the second branch 8b and, at the same time, controls or maintains the valve of the first branch in the closed condition.

Alternatively, and preferably, the management module controls the movement member 11 (preferably the piston) so as to remove the predetermined volume of air from the cuff 3.

In this way, the cuff 3 immediately loses pressure and volume, leaving that along the wall of the trachea a passage will be formed, which allows the drainage of the secretions "S".

Therefore, such "passage" allows the mucociliary clearance, without the need for intervention by the health care staff through invasive equipment.

In the preferred embodiment, the management unit 5 is configured to deflate only the first half-part 3a of the cuff 3 upon receipt of said signal.

Advantageously, in this way it is possible to minimize the passage, preferably by placing it only at the lower wall in which, when the patient "P" is in a supine position, is present almost all the secretions "S".

Preferably, the control module 9 is configured to switch the management unit 5 into said deflation configuration with a delay equal to a pre-established first time interval ΔT1 after the exceeding of a pre-established threshold value Pthresh.

In addition, the control module 9 is configured to maintain said deflation configuration for at least a second predetermined time interval ΔT2.

Such a second predetermined time interval ΔT2 is preferably less than 1.5 seconds and preferably between 0.3 and 1.5 seconds.

More precisely, the control module 9 is configured to switch the management unit 5 into said inflation configuration at the end of said second predetermined interval of time ΔT2.

Preferably, the ventilator 100, to which the apparatus 1 is connected (or integrated), comprises means of generating 101 of an overpressure.

Such means of generating 101 of an overpressure are connected to the endotracheal tube 2 through at least one connection mouth 102a, 102b.

Preferably, the ventilator includes an inlet mouth 102a and an outlet mouth 102b, both being in fluid connection with the tube 2 through respective conduits converging towards each other.

Preferably, as illustrated schematically in FIG. 1, said conduits defines an inspiratory path (connected to the mouth 102b) and an expiratory path (102a connected to the mouth), both being connected to the tube 2 through a two-input one-output connector 104.

Preferably, the connector 104 is "Y" shaped.

Moreover, the generating means 101 are configured to generate a cyclical succession of first overpressures P1 and, following one of such first overpressures, to generate a second overpressure P2 of a longer duration than said first overpressures P1 and having a value that is greater than or equal to the threshold value Pthresh mentioned above.

By way of example, the first overpressures P1 are quantifiable roughly between 15 and 30 cmH2O.

Furthermore, the second overpressure is preferably between 30 and 60 cmH2O, more preferably between 30 and 45 cmH2O.

Such second overpressure, also has a duration longer than 2 seconds, preferably of about 4 seconds.

On the contrary, each first overpressure has preferentially a duration between about 1 and 2 seconds.

Therefore, preferably, the aforementioned first time interval ΔT1 is between 0.5 and 4 seconds, more preferably between 0.5 and 1 second.

Moreover, the aforementioned second time interval ΔT2 is between 0.2 and 4 seconds, preferably about 1 second.

The succession of first overpressures P1 defines the standard breathing for the intubated patient, while the second overpressure P2 is the one commonly called "sigh", in which a higher pressure is generated in the airway with the aim of recruiting the lung and better facilitating the expulsion of the secretions "S".

Note that in defining the first overpressures P1 or the second overpressure P2 explicit reference is made to successions of waves with durations and values exemplary of the "controlled" ventilation, i.e., the ventilation in patients substantially unconscious or otherwise unable to perform a breath independently.

Considering that, it is evident that the methodology (as well as the apparatus) of the present invention is also applicable to an "assisted" mode ventilation, in which the patient is assisted in breathing by the ventilator, in which the patient, however, provides a (more or less significant) contribution.

Obviously, in this mode the ventilator will be more variable, and the generated first and second overpressures are dependent on the more or less significant contribution of the patient.

However, also in this case, the first and second overpressures will have distinguishable value and duration, falling fully in the scope of inventive methodology.

Considering that, the control module 9 is configured to switch the management unit 5 into said deflation configuration of said second overpressure P2, preferably with a delay equal to a pre-established first time interval ΔT1 after the exceeding of the pre-established threshold value.

In this light, it is noted that the sensing means 10 are preferably integrated into the ventilator 100 (or the generating means 101).

In other words, the expression "sensing means" may refers both to sensor means positioned along the line generating means-tube and software or hardware modules integrated to the ventilator 100 itself, making it possible to control the management unit 5 in open loop or closed loop.

In other words, the sensing means 10 can be defined by sensors that detect a generated pressure (closed loop) or be directly defined by the pressure generating means (open loop).

Preferably, the ventilator includes a control unit 103 associated with the generating means 101 and configured to control them.

In accordance with the above, the control unit 103 is configured to control the generating means 101 to generate a succession of overpressures P1, P2, wherein at least one of said overpressure P1, P2 has a value greater than or equal to said threshold value.

Preferably, the control unit 103 is configured to control the generating means 101 in a first mode, in which they generate the cyclical succession of first overpressures P1, and a second mode, in which they generate the second overpressure P2.

Note that the generating means 101 may directly control the pressure or act in a "volumetric" mode; for simplicity of description, in the present text waveforms are illustrated that are generated with a "pressometric control", but this is not to be limiting in any way and also encompasses generating means 101 configured to control the pressure in the volumetric mode (with more inclined/beveled rising edges).

Therefore, the control unit 103 is configured to maintain said second mode of the generating means 101 for a period of time between an initial instant and a final instant, in which preferably the period of time is greater than 2 seconds, as mentioned above.

According to an aspect of the invention, the control unit 103 is associated with or comprises the control module 9 of the apparatus 1, in order to control the management unit 5 on the basis of a condition of the generating means 101.

Preferably, the control unit 103 includes the control module 9.

Therefore, the control module 9 is configured to switch the management unit 5 into said deflation configuration when the generating means 101 generates said overpressure having a higher value than the threshold value.

Preferably, the control module 9 is configured to switch the management unit 5 into the deflation configuration when the generating means 101 are in said second mode.

Preferably, the control module 9 is thus configured to switch the management unit 5 into said deflation configuration with an initial instant delay equal to the predetermined first time interval ΔT1 (more preferably keeping it for the second time interval ΔT2).

In certain embodiments, the ventilator 100 also comprises suction means (not shown) and a catheter slidingly insertable in the endotracheal tube 2.

The control unit 103 is in turn associated with such suction means (possibly drivable manually by the operator) to perform aspiration of the secretions "S" in the bronchopulmonary zone more distant from the cuff 3, namely the zone in which the only deflation of the cuff 3 would have no effect.

Preferably, such a suction is performed before the step of cuff 3 deflation.

In this way, there would be a more complete removal of the secretions "S".

In the preferred embodiment, the tube 2 is associated to a further conduit 12 (also preferably integrated with the side wall 2c).

More precisely, this further conduit 12 extends along the first portion 4a of the tube 2 and opens into an end section located immediately upstream of the cuff 3, facing the outside of the tube 2.

This further conduit 12 is in fluid connection with the suction means (not shown), which can be integrated or not with the ventilator 100, configured to generate a depression and to aspirate, through said further conduit 12, the secretions in the subglottic zone.

Preferably, also the suction means are associated to the control unit 103.

More precisely, the control unit 103 is configured to activate the suction means before, during, or immediately after the generation of said second overpressure P2.

Therefore, the control unit is configured to activate the suction means 103 in conjunction with the switching of the management means in the deflation configuration.

In the preferred embodiment, the control unit is configured to keep active the suction means during all of said generation of the second overpressure P2.

Advantageously, in this way it is possible to extract any residual secretions in the subglottic zone, preventing their flow back towards the distal zone during the deflation, and facilitating simultaneously the aspiration of the secretions "S" towards the not-sterile zone Z2.

The apparatus 1 and the ventilator 100 described so far are therefore adapted to implement the method for the management of secretions in an intubated patient "P" by means of an endotracheal tube 2, which is the primary object of the present invention.

Indeed, this method comprises the step of inflating the inflatable cuff 3 to isolate the bronchopulmonary zone of the patient "P" from the outside environment;

The inflation volume of the cuff 3 is to be determined according to type of patient and is therefore proportional to the size of the trachea and correlated to a target pressure to be generated in the cuff 3; however, the pressure inside the cuff 3 is determined independently of the volume.

Indicatively, the maximum pressure within the cuff, in order to prevent ischemia, is between 20 and 30 cmH2O.

A further step is provided that comprises generating a succession of overpressures P1, P2 inside the endotracheal tube 2 in order to induce breathing in the patient.

More precisely, it is expected to generate a cyclical succession of first overpressures P1 inside the endotracheal tube 2 in order to induce breathing in the patient "P".

Preferably, such overpressures are generated by means of a positive-pressure ventilator, more preferably by means of a ventilator 100 of the type described hitherto.

Downstream of one of said first overpressure, the method provides a generation of a second overpressure P2 inside the tube 2, of a duration and a value exceeding that of said first overpressures P1, in order to recruit the lungs of the patient "P".

The preferential parameters and examples of the above first and second overpressures have been defined previously, in relation to the apparatus 1 and to the ventilator 100, and remain the same, without implying any limitation, also for the method of the invention.

Also, note that the overpressures are defined to be generated inside the tube 2, although the primary purpose is to establish them within the airways of the patient "P", and consequently of the lung.

This is mainly because, as already described above, the tube is in fluid connection with the airways, in particular with the broncho-pulmonary zone of interest (i.e., pressure-tight environment "Z").

According to one aspect of the present invention, the method provides a step of deflating the inflatable cuff 3 (or at least part thereof) during the generation of one of said overpressures (P1, P2) in order to permit a drainage of secretions "S" generated by the patient "P" along the trachea towards the outside.

Preferably, the step of deflation is performed during said generation of the second overpressure in order to permit a drainage of the generated secretions "S" by the patient "P" along the trachea, from the bronchus-lung zone towards the outside.

More precisely, as mentioned earlier, the step of generating the second overpressure is performed during a period of time between an initial instant and a final instant (preferably with a duration longer than 2 seconds).

The deflation step of the inflatable cuff 3 preferably starts with a delay equal to a pre-established first time interval ΔT1 from the initial instant.

Furthermore, the deflation step of deflating preferably has a duration equal to a second time interval ΔT2.

To ensure the complete sealing of the pressurized environment, i.e. the sealing of the cuff 3, preferably the final instant of the second generation of overpressure phase is delayed, compared to the end of deflation step, by a third time interval ΔT3.

Advantageously, in this way the management unit 5 has the time to bring back the cuff 3 to the correct pressure before the pressure can fall in the airways, preventing a reflux of secretions "S" (or other secretions already present in the trachea).

Preferably, it should be noted that the deflation step only provides the deflation of the first half-part 3a of said cuff 3, while keeping the second half-part 3b inflated and adhered to the trachea of the patient's "P".

Advantageously, this optimizes the method performance and makes it safer.

Preferably, moreover, in order to maximize the removal of the secretions "S", especially in those patients in which the same are particularly dense, the method provides a step of aspiration of secretions located downstream of the endotracheal tube 2, which is performed upstream of said deflation step.

Preferably, in accordance with what is described above, the suction step is carried out through a further tube or catheter slidably inserted in said endotracheal tube 2.

In the preferred embodiment, the method provides a step of subglottic suction performed immediately upstream of and/or during said cuff 3 deflation.

Preferably, this aspiration is carried out during the whole step of generation of the second overpressure P2.

Preferably, the aspiration provides to generate a reduce pressure of about 20 cmH2O or similar values (to be adjusted from patient to patient).

Advantageously, as described above, in this way it is possible to extract any residual secretions in the subglottic zone, preventing their flow back towards the distal zone during the deflation, and facilitating simultaneously the movement of the secretions "S" towards the not-sterile zone "Z2".

In a further preferred embodiment, the method comprises a step of filtering or storing the air contained in the non-sterile zone in order to avoid the spread of bacteria contained in said secretions "S".

In other words, the method provides to isolate or filter the zone containing the secretions "S" expelled from the sterile zone (or from the broncho-pulmonary zone) in order to prevent the spread of microorganisms such as bacteria or viruses.

This step can be done by using masks or by a further suction.

The invention achieves the intended objects and achieves important advantages.

In fact, thanks to the method described and claimed herein, namely thanks to deflation of the cuff simultaneously with the overpressure in the airways, it is possible exploit and aid, in a natural way, the mucociliary clearance in intubated patients, without the need of using invasive and painful interventions (such as aspirations).

Furthermore, the possibility to program the control unit of already known ventilators to operate such innovative methodology, makes the same easily accessible and of economical construction.

The invention claimed is:

1. An apparatus for controlling a pressure in an endotracheal cuff associable with a positive-pressure ventilator, comprising:
   an endotracheal tube;
   an inflatable cuff positioned along the endotracheal tube so as to divide an outer surface of the endotracheal tube into a first portion, which is proximal during use, and a second portion, which is distal during use;
   a pressure management unit placed in fluid connection with the inflatable cuff and selectively switchable between an inflation configuration, in which the pressure management unit inflates and/or maintains inflated the inflatable cuff, and a deflation configuration, wherein the pressure management unit deflates the inflatable cuff;
   a pressure sensing device configured to detect a pressure correlated with or representative of a pulmonary pressure of an intubated patient;
   a control module operatively connected with the pressure management unit and with the pressure sensing device and configured to control the pressure management unit on a basis of a signal read by the pressure sensing device;
   wherein the control module is programmed to switch the pressure management unit into the deflation configuration upon receipt, by the pressure sensing devices, of a threshold signal representative of exceeding of a pre-established threshold value (Pthresh) of the detected pulmonary pressure in order to enable a drainage of secretions, outside the endotracheal tube, generated by the intubated patient, from the second portion to the first portion.

2. The apparatus according to claim 1, wherein the control module is configured to switch the pressure management unit into the deflation configuration with a delay equal to a pre-established first time interval (ΔT1) after the exceeding of the pre-established threshold value (Pthresh).

3. The apparatus according to claim 1, wherein the control module is configured to maintain the deflation configuration for at least a second predetermined time interval (ΔT2) and to switch the pressure management unit into the deflation configuration at an end of the second predetermined time interval (ΔT2).

4. The apparatus according to claim 1, wherein the inflatable cuff is divided into a first half-part and a second half-part isolated from each other, wherein the pressure management unit is configured to deflate only the first half-part upon receipt of the signal representative of exceeding of the pre-established threshold value (Pthresh).

5. The apparatus according to claim 1, wherein the pressure management unit includes a generating device including a pump for generating a pressure in the inflatable cuff and a releasing device for releasing pressure from the inflatable cuff.

6. The apparatus according to claim 5, wherein the control module includes a controller, a memory and programming programmed into the memory to control the controller.

7. The apparatus according to claim 1, wherein the control module includes a controller, a memory and programming programmed into the memory to control the controller.

8. A positive-pressure ventilator for artificial ventilation of an intubated patient, comprising:
   the apparatus according to claim 1;
   an outlet port operatively connected with an overpressure generating device;
   a control unit operatively connected with the overpressure generating device and configured to control the overpressure generating device in a cyclical manner;
   wherein:
   the endotracheal tube is connected to the outlet port;

the control unit is operatively connected with or comprises the control module in order to control the pressure management unit on a basis of a condition of the overpressure generating device.

9. The positive-pressure ventilator according to claim 8, wherein the control unit is configured to control the overpressure generating device so as to generate a succession of overpressures, wherein at least one of the overpressures has a value greater than or equal to the pre-established threshold value; the control module being configured to switch the pressure management unit into the deflation configuration when the overpressure generating device generates the at least one of the overpressures having the value greater than or equal to the pre-established threshold value.

10. The positive-pressure ventilator according to claim 8, wherein the control unit is configured to control the overpressure generating device in a first mode, in which the overpressure generating device generates a cyclical succession of first overpressures, and a second mode, in which the overpressure generating device generates a second overpressure of a longer duration than the first overpressures and having a value that is greater than or equal to the pre-established threshold value; the control module being configured to switch the pressure management unit into the deflation configuration when the overpressure generating device is in the second mode.

11. The positive-pressure ventilator according to claim 10, wherein the control unit is configured to maintain the second mode of the overpressure generating device for a period of time between an initial instant and a final instant;
the control module being configured to switch the pressure management unit into
the deflation configuration with a delay equal to a pre-established time interval ($\Delta T1$) from the initial instant.

12. The positive-pressure ventilator according to claim 8, wherein the pressure management unit includes a generating device including a pump for generating a pressure in the inflatable cuff and a releasing device for releasing pressure from the inflatable cuff and the control module includes a controller, a memory and programming programmed into the memory to control the controller.

13. An apparatus for controlling a pressure in an endotracheal cuff associable with a positive-pressure ventilator, comprising:
an endotracheal tube;
an inflatable cuff positioned along the endotracheal tube so as to divide an outer surface of the endotracheal tube into a first portion, which is proximal during use, and a second portion, which is distal during use;
a pressure management unit, including an aspirating and pumping volumetric device, or a pumping volumetric device and a venting conduit or a valve, for generating and releasing a pressure in the inflatable, placed in fluid connection with the inflatable cuff and selectively switchable between an inflation configuration, in which the pressure management unit inflates and/or maintains inflated the inflatable cuff, and a deflation configuration, wherein the pressure management unit deflates the inflatable cuff;
a pressure sensing device configured to detect a pressure correlated with or representative of a pulmonary pressure of an intubated patient;
a control module operatively connected with the pressure management unit and with the pressure sensing device and configured to control the pressure management unit on a basis of a signal read by the pressure sensing device;
wherein the control module includes a controller, a memory and programming programmed into the memory to control the controller, the control module being configured and programmed to switch the pressure management unit into the deflation configuration upon receipt, by the pressure sensing device, of a threshold signal representative of exceeding of a pre-established threshold value (Pthresh) of the detected pulmonary pressure in order to enable a drainage of secretions, outside the endotracheal tube, generated by the intubated patient, from the second portion to the first portion.

14. The apparatus according to claim 13, wherein the control module is configured to switch the pressure management unit into the deflation configuration with a delay equal to a pre-established first time interval ($\Delta T1$) after the exceeding of the pre-established threshold value (Pthresh).

15. The apparatus according to claim 13, wherein the control module is configured to maintain the deflation configuration for at least a second predetermined time interval ($\Delta T2$) and to switch the pressure management unit into the deflation configuration at an end of the second predetermined time interval ($\Delta T2$).

16. The apparatus according to claim 13, wherein the inflatable cuff is divided into a first half-part and a second half-part isolated from each other, wherein the pressure management unit is configured to deflate only the first half-part upon receipt of the signal representative of exceeding of the pre-established threshold value (Pthresh).

17. A positive-pressure ventilator for artificial ventilation of an intubated patient, comprising:
the apparatus according to claim 13;
an outlet port operatively connected with an overpressure generating device;
wherein:
the endotracheal tube is connected to the outlet port;
the control unit is operatively connected with or comprises the control module in order to control the pressure management unit on a basis of a condition of the overpressure generating device.

18. The positive-pressure ventilator according to claim 17, wherein the control unit is configured to control the overpressure generating device so as to generate a succession of overpressures, wherein at least one of the overpressures has a value greater than or equal to the pre-established threshold value; the control module being configured to switch the pressure management unit into the deflation configuration when the overpressure generating device generates the at least one of the overpressures having the value greater than or equal to the pre-established threshold value.

19. The positive-pressure ventilator according to claim 17, wherein the control unit is configured to control the overpressure generating device in a first mode, in which the overpressure generating device generates a cyclical succession of first overpressures, and a second mode, in which the generating device generates a second overpressure of a longer duration than the first overpressures and having a value that is greater than or equal to the pre-established threshold value; the control module being configured to switch the pressure management unit into the deflation configuration when the overpressure generating device is in the second mode.

20. The positive-pressure ventilator according to claim 19, wherein the control unit is configured to maintain the second mode of the overpressure generating device for a period of time between an initial instant and a final instant;
the control module being configured to switch the pressure management unit into the deflation configuration with a delay equal to a pre-established time interval ($\Delta T1$) from the initial instant.

\* \* \* \* \*